US00PP18916P2

(12) United States Plant Patent
Smith

(10) Patent No.: US PP18,916 P2
(45) Date of Patent: Jun. 10, 2008

(54) ***CHRYSANTHEMUM* PLANT NAMED 'YOASHLEY'**

(50) Latin Name: *Chrysanthemum×morifolium*
Varietal Denomination: Yoashley

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/641,395

(22) Filed: Dec. 18, 2006

(51) Int. Cl.
*A01H 5/00* (2006.01)

(52) U.S. Cl. ..... Plt./290

(58) Field of Classification Search ..... Plt./290
See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Chrysanthemum* plant named 'Yoashley', characterized by its compact, upright and outwardly spreading plant habit; freely branching habit; dense and full plant habit; uniform and freely flowering habit; decorative-type inflorescences with elongated oblong to obovate-shaped ray florets; dark orange-colored ray florets; and natural season flowering about October 6$^{th}$ in the Northern Hemisphere.

1 Drawing Sheet

Botanical designation: *Chrysanthemum×morifolium.*
Cultivar denomination: 'YOASHLEY'.

BACKGROUND OF THE INVENTION

The present invention relates to a new and distinct cultivar of *Chrysanthemum* plant, botanically known as *Chrysanthemum×morifolium,* commercially grown as a garden *Chrysanthemum* and hereinafter referred to by the name 'Yoashley'.

The objective of the breeding program is to create new garden-type *Chrysanthemum* cultivars having inflorescences with desirable inflorescence forms, attractive floret colors and good garden performance.

The new *Chrysanthemum* originated from a cross-pollination made by the Inventor in February, 2002, in Salinas, Calif. of a proprietary selection of *Chrysanthemum×morifolium* identified as code number 98-M306, not patented, as the female, or seed, parent with the *Chrysanthemum×morifolium* cultivar Jessica, disclosed in U.S. Plant Pat. No. 7,587, as the male, or pollen, parent. The new Chrysanthemum was discovered and selected by the Inventor as a single flowering plant within the progeny of the stated cross-pollination in a controlled environment in Alva, Fla. in November, 2002.

Asexual reproduction of the new *Chrysanthemum* by vegetative cuttings was first conducted in Alva, Fla. in January, 2003. Asexual reproduction by cuttings has shown that the unique features of this new Chrysanthemum are stable and reproduced true to type in successive generations.

SUMMARY OF THE INVENTION

Plants of the cultivar Yoashley have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yoashley'. These characteristics in combination distinguish 'Yoashley' as a new and distinct garden *Chrysanthemum* cultivar:

1. Compact, upright and outwardly spreading plant habit.
2. Freely branching habit; dense and full plant habit.
3. Uniform and freely flowering habit.
4. Decorative-type inflorescences with elongated oblong to obovate-shaped ray florets.
5. Dark orange-colored ray florets.
6. Natural season flowering about October 6$^{th}$ in the Northern Hemisphere.

In side-by-side comparisons conducted in Alva, Fla., plants of the new *Chrysanthemum differed from* plants of the female parent selection in the following characteristics:

1. Plants of the new *Chrysanthemum* were larger and more uniformly mounded than plants of the female parent selection.
2. Plants of the new *Chrysanthemum* flowered later than plants of the female parent selection when grown under natural season conditions.
3. Plants of the new *Chrysanthemum* had smaller inflorescences than plants of the female parent selection.
4. Plants of the new *Chrysanthemum* and the female parent selection differed in ray floret color as plants of the female parent selection had bronze-colored ray florets.

In side-by-side comparisons conducted in Alva, Florida, plants of the new *Chrysanthemum* differed from plants of the male parents, the cultivar Jessica, in the following characteristics:

1. Plants of the new *Chrysanthemum* were more mounded than plants of the cultivar Jessica.
2. Plants of the new *Chrysanthemum* flowered more uniformly and later than plants of the cultivar Jessica when grown under natural season conditions.

3. Plants of the new *Chrysanthemum* and the cultivar Jessica differed in ray floret color as plants of the cultivar Jessica had yellow-colored ray florets.

Plants of the new *Chrysanthemum* can be compared to plants of the *Chrysanthemum* cultivar Yosherry, disclosed in U.S. Plant Pat. No. 17,601. In side-by-side comparisons conducted in Alva, Fla. plants of the new *Chrysanthemum* differed primarily from plants of the cultivar Yosherry in the following characteristics:

1. Plants of the new *Chrysanthemum* were larger than plants of the cultivar Yosherry.
2. Inflorescences of plants of the new *Chrysanthemum* lasted longer then inflorescences of plants of the cultivar Yosherry.
3. Ray florets of plants of the new *Chrysanthemum* were lighter in color than ray florets of plants of the cultivar Yosherry.

BRIEF DESCRIPTION OF THE PHOTOGRAPHS

The accompanying photographs illustrate the overall appearance of the new *Chrysanthemum*. These photographs show the colors as true as it is reasonable possible to obtain in colored reproductions of this type. Colors in the photographs may differ slightly from the color values cited in the detailed botanical description which accurately describe the colors of the new *Chrysanthemum*.

The photograph at the bottom of the sheet comprises a side perspective view of a typical flowering plant of 'Yoashley'.

The photograph at the top of the sheet is a close-up view of typical inflorescences of 'Yoashley'.

DETAILED BOTANICAL DESCRIPTION

The aforementioned photographs and following observations and measurements describe plants grown in Fletcher, N.C. during the summer in an outdoor nursery and under conditions and practices which approximate those generally used in commercial garden *Chrysanthemum* production. During the production of the plants, day temperatures averaged 29° C. and night temperatures averaged 16° C. Plants were grown in 15-containers, exposed to long day/short night conditions and pinched about two weeks later. About two weeks after the pinch, the photoinductive short day/long night treatments were started. Plants the photoinductive short day/long night treatments were started. Plants used in the photographs and for the description were about three months old. In the following description, color references are made to The Royal Horticultural Society Colour Chart, 1995 Edition, except where general terms of ordinary dictionary significance are used.

Botanical classification: *Chrysanthemum×morifolium* cultivar Yoashley.

Parentage:

*Female, or seed, parent.*—Proprietary selection of *Chrysanthemum×morifolium* identified as code number 98-M306, not patented.

*Male, or pollen, parent—Chrysanthemum×morifolium* cultivar Jessica, disclosed in U.S. Plant Pat. No. 7,587.

Propagation:

*Type.*—Terminal vegetative cuttings.

*Time to initiate roots.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Herbaceous decorative-type garden *Chrysanthemum*. Stems upright and outwardly spreading giving a uniformly mounded appearance to the plant. Freely branching habit, about five to size lateral branches develop after removal of terminal apex (pinching) each with numerous secondary laterals; dense and full plant habit. Strong and vigorous growth habit.

*Plant height.*—About 20 cm.

*Plant width.*—About 27 cm.

*Lateral branches.*—Length: About 18 cm. Diameter: About 7 mm. Internode length: About 1.2 cm. Strength: Strong. Texture: Pubescent. Color: 147B.

*Leaves.*—Arrangement: Alternate, simple. Length: About 4 cm. Width: About 3.2 cm. Apex: Rounded to cuspidate. Base: Attenuate. Margin: Palmately lobed, sinuses between lateral lobes mostly divergent. Texture, upper and lower surfaces: Fine pubescence; veins prominent on lower surface. Color: Developing and fully expanded foliage, upper surface: 147A; venation, 147C. Developing and fully expanded foliage, lower surface: 147B; venation, 147C. Petiole: Length: About 1.6 cm. Diameter: About 3 mm. Texture, upper and lower surfaces: Pubescent. Color, upper and lower surfaces: 147B.

Inflorescence description:

*Appearance.*—Decorative-type inflorescence form with elongated oblong to obovate-shaped ray florets. Inflorescences borne on terminals above foliage. Disk and ray florets arranged acropetally on a capitulum. Inflorescences faintly fragrant.

*Flowering response.*—Under natural season conditions, plants flower about October 6$^{th}$ in the Northern Hemisphere. At other times of the year, inflorescence initiation and development can be induced under short day/long night conditions (at least 13.5 hours of darkness). Early flowering habit; plants exposed to photoinductive short day/long night conditions flower about 51 days later.

*Postproduction longevity.*—Inflorescences maintain good color and substance for about four weeks in an outdoor nursery.

*Quantity of inflorescences.*—About 24 inflorescences develop per lateral branch.

*Inflorescence bud.*—Height: About 1.2 cm. Diameter: About 1 cm. Shape: Ovoid. Color: 14B.

*Inflorescence size: Diameter: About* 3.2 cm. Depth (height): About 1.5 cm. Receptacle diameter: About 1.5 cm. Receptacle height: About 3 mm.

*Ray florets.*—Shape: Elongated-oblong to obovate. Orientation: Initially upright, then about 90° from vertical or perpendicular to the peduncle. Aspect: Initially incurved, then mostly concave. Length: About 1.5 cm. Width: About 5 mm. Apex: Emarginate. Base: Acute. Margin: Entire. Texture, upper and lower surfaces: Smooth, glabrous, satiny. Number of ray florets per inflorescence: About 174 arranged in about ten to twelve whorls. Color: When opening, upper surface: 169C. When opening, lower surface: 173C. Fully opened, upper surface: 172A. Fully opened, lower surface: 174C.

*Disc florets.*—No disc florets observed.

*Phyllaries.*—Number of phyllaries per inflorescence: About 22 arranged in about two whorls. Length: About 5 mm. Width: About 3 mm. Shape: Elliptical. Apex: Acute. Base: Truncate. Texture, upper surface: Smooth, waxy. Texture, lower surface: Pubescent. Color, upper surface: Close to 147A. Color, lower surface: Close to 147B.

*Peduncles.*—Length: About 5.3 cm. Diameter: About 2 mm. Angle: About 45° from vertical. Strength: Strong. Texture: Pubescent; longitudinally ridged. Color: Close to 148A.

*Reproductive organs.*—Androecium: None observed. Gynoecium: Pistil length: About 6 mm. Stigma shape: Bi-parted. Stigma color: Close to 5A. Style length: About 3 mm. Style color: Close to 1B. Ovary color: Close to 157A.

*Seed/fruit.*—Seed and fruit production has not been observed.

Disease/pest resistance: Resistance to pathogens and pets common to *Chrysanthemums* has not been observed on plants grown under commercial conditions.

Garden performance: Plants of the new *Chrysanthemum* have demonstrated excellent garden performance and to tolerate temperatures from about 0° C. to about 38° C.

It is claimed:

1. A new and distinct *Chrysanthemum* plant named 'Yoashley' as illustrated and described.

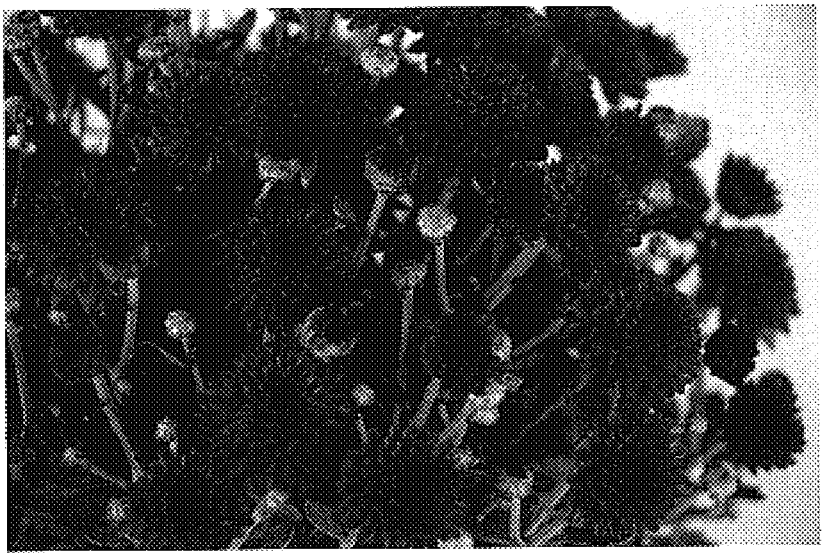
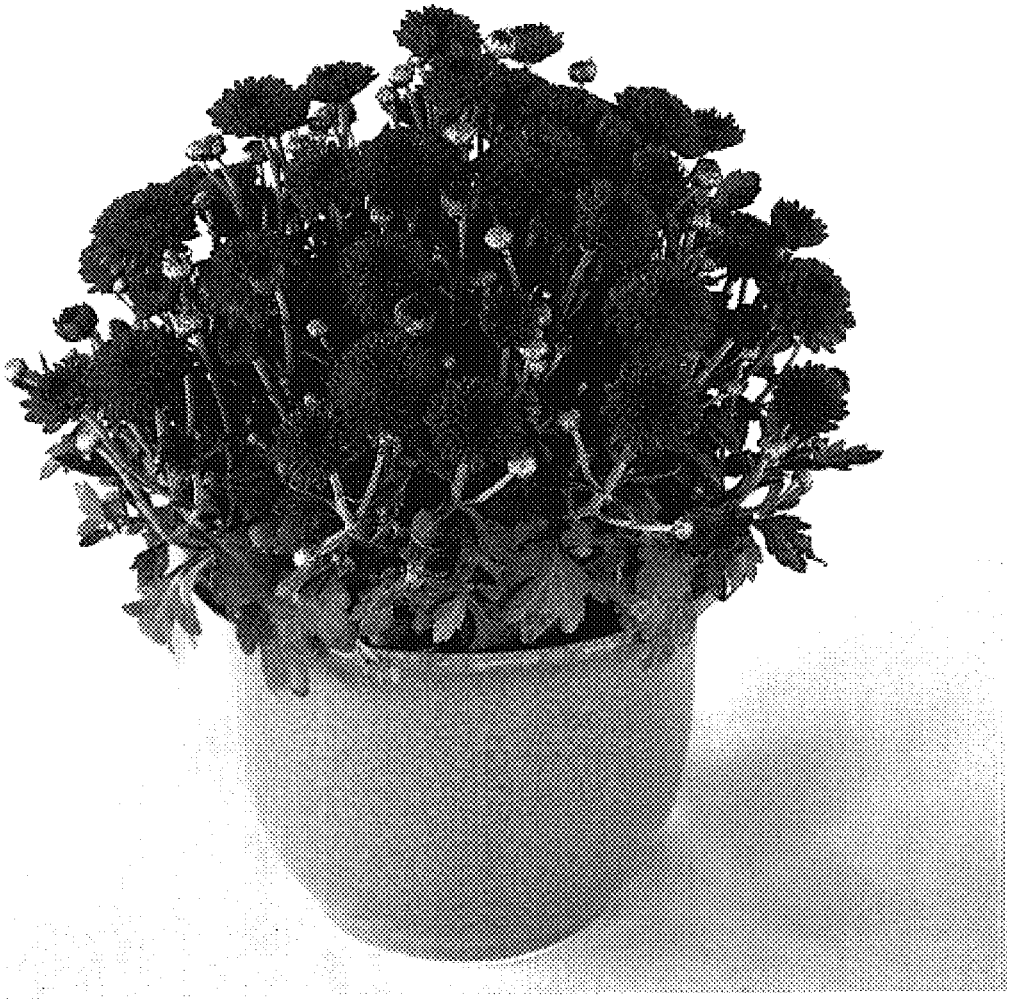

* * * * *